United States Patent
Torrianni

(10) Patent No.: US 6,509,145 B1
(45) Date of Patent: Jan. 21, 2003

(54) PROCESS FOR REDUCING MINERALIZATION OF TISSUE USED IN TRANSPLANTATION

(75) Inventor: Mark W. Torrianni, San Juan Capistrano, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/806,380

(22) PCT Filed: Sep. 30, 1999

(86) PCT No.: PCT/US99/22550

§ 371 (c)(1),
(2), (4) Date: Mar. 30, 2001

(87) PCT Pub. No.: WO00/18445

PCT Pub. Date: Apr. 6, 2000

Related U.S. Application Data

(60) Provisional application No. 60/102,514, filed on Sep. 30, 1998, provisional application No. 60/103,697, filed on Oct. 9, 1998, and provisional application No. 60/105,949, filed on Oct. 28, 1998.

(51) Int. Cl.[7] ............................ A01N 1/00; A01N 1/02; A61F 2/00
(52) U.S. Cl. ........................................ 435/1.1; 424/423
(58) Field of Search ............................ 435/1.1; 424/423

(56) References Cited

U.S. PATENT DOCUMENTS

| | | | |
|---|---|---|---|
| 4,378,224 A | 3/1983 | Nimni et al. ................. 8/94.11 |
| 4,553,974 A * | 11/1985 | Dewanjee | |
| 4,647,283 A | 3/1987 | Carpentier et al. ........... 623/11 |
| 4,648,881 A | 3/1987 | Carpentier et al. ........... 623/11 |
| 4,753,652 A | 6/1988 | Langer et al. ................. 623/1 |
| 4,755,593 A | 7/1988 | Lauren ....................... 530/356 |
| 4,786,287 A | 11/1988 | Nashef et al. ............... 8/94.11 |
| 4,838,888 A | 6/1989 | Nashef ......................... 623/2 |
| 4,976,733 A | 12/1990 | Girardot ....................... 623/11 |
| 5,094,661 A | 3/1992 | Levy et al. ................... 8/94.11 |
| 5,104,405 A | 4/1992 | Nimni ........................... 623/2 |
| 5,147,514 A | 9/1992 | Mechanic .............. 204/157.68 |
| 5,296,583 A | 3/1994 | Levy ............................ 528/72 |
| 5,300,306 A | 4/1994 | Alvarado et al. ........... 424/550 |
| 5,332,475 A | 7/1994 | Mechanic .............. 204/157.68 |
| 5,368,608 A | 11/1994 | Levy et al. .................. 8/94.11 |
| 5,397,353 A | 3/1995 | Oliver et al. ................. 623/11 |
| 5,413,798 A * | 5/1995 | Scholl et al. | |
| 5,436,291 A | 7/1995 | Levy et al. .................. 524/706 |
| 5,437,287 A | 8/1995 | Phillips et al. .............. 128/898 |
| 5,447,536 A | 9/1995 | Girardot et al. ............. 8/94.11 |
| 5,476,516 A | 12/1995 | Seifter et al. ................ 8/94.11 |
| 5,509,932 A | 4/1996 | Keogh et al. ................. 623/11 |
| 5,578,314 A | 11/1996 | Cochrum et al. ........... 424/424 |
| 5,595,571 A | 1/1997 | Jaffe et al. .................... 8/94.11 |
| 5,645,587 A | 7/1997 | Chanda et al. ................ 623/11 |
| 5,674,298 A | 10/1997 | Levy et al. ................... 8/94.11 |
| 5,679,112 A | 10/1997 | Levy et al. ................... 8/94.11 |
| 5,697,972 A | 12/1997 | Kim et al. ..................... 623/2 |
| 5,720,777 A | 2/1998 | Jaffe et al. ..................... 623/2 |
| 5,733,339 A | 3/1998 | Girardot et al. ............. 8/94.11 |
| 5,746,778 A | 5/1998 | Levy et al. ................... 8/94.11 |
| 5,782,931 A | 7/1998 | Yang et al. ................... 8/94.11 |
| 5,824,067 A | 10/1998 | Gross ............................. 623/2 |
| 5,891,196 A | 4/1999 | Lee et al. ..................... 8/94.11 |
| 5,916,265 A * | 6/1999 | Hu | |
| 5,989,498 A | 11/1999 | Odland ........................ 422/22 |
| 6,093,530 A | 7/2000 | McIlroy et al. .............. 422/1.1 |
| 6,166,184 A | 12/2000 | Hendriks et al. ........... 530/356 |
| 6,203,755 B1 | 3/2001 | Odland ........................ 422/22 |
| 6,251,579 B1 * | 6/2001 | Moore et al. | |

FOREIGN PATENT DOCUMENTS

| | | |
|---|---|---|
| EP | 0 172 716 | 8/1985 |
| WO | 84/01879 | 5/1984 |
| WO | 89/06945 | 8/1989 |

* cited by examiner

*Primary Examiner*—Christopher R. Tate
(74) *Attorney, Agent, or Firm*—Thomas G. Berry; Daniel W. Latham

(57) ABSTRACT

A method of making a tissue-derived implantable medical device that includes contacting the tissue with a composition comprising at least one oxidizing agent prior to implantation of the medical device.

57 Claims, No Drawings

PROCESS FOR REDUCING MINERALIZATION OF TISSUE USED IN TRANSPLANTATION

CROSS-REFERENCE TO RELATED APPLICATIONS

The present application claims priority to Provisional Application No. 60/102,514, filed Sep. 30, 1998, No. 60/103,697, filed Oct. 9, 1998, and No. 60/105,949, filed Oct. 28, 1998, all of which are incorporated herein by reference.

BACKGROUND OF THE INVENTION

The surgical implantation of prosthetic devices (prostheses) into humans and other mammals has been carried out with increasing frequency. Such prostheses include, by way of illustration, heart valves, vascular grafts, urinary bladders, heart bladders, left ventricular-assist devices, and the like. The prostheses may be constructed from natural tissues, inorganic materials, synthetic polymers, or combinations thereof. By way of illustration, mechanical heart valve prostheses typically are composed of rigid materials, such as polymers, carbon-based materials, and metals. Valvular bioprostheses, on the other hand, typically are fabricated from either porcine aortic valves or bovine pericardium.

Prostheses derived from natural tissues are preferred over mechanical devices because of certain clinical advantages. For example, tissue-derived prostheses generally do not require routine anticoagulation. Moreover, when tissue-derived prostheses fail, they usually exhibit a gradual deterioration which can extend over a period of months or even years. Mechanical devices, on the other hand, typically undergo catastrophic failure.

Although any prosthetic device can fail because of mineralization, such as calcification, this cause of prosthesis degeneration is especially significant in tissue-derived prostheses. Indeed, calcification has been stated to account for 50 percent of failures of cardiac bioprosthetic valve implants in children within 4 years of implantation. In adults, this phenomenon occurs in approximately 20 percent of failures within 10 years of implantation. See, for example, Schoen et al., *J. Lab. Invest.*, 52, 523–532 (1985). Despite the clinical importance of the problem, the pathogenesis of calcification is not completely understood. Moreover, there apparently is no effective therapy known at the present time.

The origin of mineralization, and calcification in particular, has, for example, been shown to begin primarily with cell debris present in the tissue matrices of bioprosthetic heart valves, both of pericardial and aortic root origin. Bioprosthetic cross-linked tissue calcification has also been linked to the presence of alkaline phosphatase that is associated with cell debris and its possible accumulation within implanted tissue from the blood. Still others have suggested that mineralization is a result of phospholipids in the cell debris that sequester calcium and form the nucleation site of apatite (calcium phosphate).

Regardless of the mechanism by which mineralization in bioprostheses occurs, mineralization, and especially calcification, is the most frequent cause of the clinical failure of bioprosthetic heart valves fabricated from porcine aortic valves or bovine pericardium. Human aortic homograft implants have also been observed to undergo pathologic calcification involving both the valvular tissue as well as the adjacent aortic wall albeit at a slower rate than the bioprosthetic heart valves. Pathologic calcification leading to valvular failure, in such forms as stenosis and/or regeneration, necessitates re-implantation. Therefore, the use of bioprosthetic heart valves and homografts have been limited because such tissue is subject to calcification. In fact, pediatric patients have been found to have an accelerated rate of calcification so that the use of bioprosthetic heart valves is contraindicated for this group.

Several possible methods to decrease or prevent bioprosthetic heart valve mineralization have been described in the literature since the problem was first identified. Generally, these methods involve treating the bioprosthetic valve with various substances prior to implantation. Among the substances reported to work are sulfated aliphatic alcohols, phosphate esters, amino diphosphonates, derivatives of carboxylic acid, and various surfactants. Nevertheless, none of these methods have proven completely successful in solving the problem of post-implantation mineralization.

Currently there are no bioprosthetic heart valves that are free from the otential to mineralize in vivo. Although there is a process employing amino oleic acid (AOA) as an agent to prevent calcification in the leaflets of porcine aortic root tissue used as a bioprosthetic heart valve, AOA has not been shown to be effective in preventing the mineralization of the aortic wall of such devices. As a result, such devices may have to be removed.

Accordingly, there is a need for providing long-term calcification resistance for bioprosthetic heart valves and other tissue-derived implantable medical devices which are subject to in vivo pathologic calcification.

SUMMARY OF THE INVENTION

The present invention provides a method for reducing the level of mineralization of tissue in a tissue-derived implantable medical device. Preferably, the method reduces the level of bioprosthetic valvular mineralization, and in particular bioprosthetic valvular pathologic calcification.

In a preferred embodiment of the invention, the tissue-derived implantable medical device treated by a method of the invention exhibits improved anti-mineralization properties, and/or longer term resistance to in vivo pathologic calcification than provided by other methods of reducing and/or preventing mineralization. Although not wishing to be bound by theory, the method of the invention may inhibit enzymes and other proteins (e.g., calcium binding proteins) that are present within the tissue from performing their specific functions. These proteins are principally involved in phosphate and calcium metabolism and may be important in the formation of calcium phosphate, the major component of mineralized tissue. Treatment by the method of the invention may effectively inactivate such protein activity and reduce the accumulation of phosphates and/or calcium in the tissue after implantation, thus reducing the initiation of the mineralization process.

In another preferred embodiment, the method provides treatments performed on tissue during a method of making a tissue-derived implantable medical device. These treatment steps can be performed immediately upon excision of tissue from an animal, for example, or subsequent to incorporating the tissue into the device. A preferred device is a bioprosthetic heart valve. The method reduces mineralization on valvular leaflets and supporting structures, such as the aortic walls, after the device is implanted into patients. Reduction of mineralization of both valvular leaflets and aortic walls may allow for improved performance of the device over the duration of the implant.

In one embodiment, the present invention provides a method of making a tissue-derived implantable medical device. The method involves contacting the tissue with a composition that includes at least one oxidizing agent prior to implantation of the medical device. Preferably, the method further includes rinsing the tissue to remove at least a portion of, and preferably substantially all of, the oxidizing agent. Preferably, the tissue-derived implantable medical device is a heart valve, which can be derived from porcine aortic root tissue, bovine aortic root tissue, porcine pericardium, bovine pericardium, bovine veins, porcine veins, bovine arteries, or porcine arteries.

Preferably, the oxidizing agent is selected from the group of sodium hypochlorite, sodium bromate, sodium hydroxide, sodium iodate, sodium periodate, performic acid, periodic acid, potassium dichromate, potassium permanganate, chloramine T, peracetic acid, and combinations thereof. More preferably, the oxidizing agent is selected from the group of sodium hypochlorite, performic acid, periodic acid, peracetic acid, and combinations thereof.

The composition that includes an oxidizing agent preferably further includes at least one chelating agent. Examples of suitable chelating agents include ethylenediaminetetraacetic acid (EDTA), ethylenebis(oxyethylenenitrilo) tetraacetic acid (EGTA), citric acid, salts thereof, and combinations thereof.

The composition that includes an oxidizing agent also preferably further includes a buffer (i.e., buffering agent). Preferably, the buffer has a pKa of about 7.0 to about 7.5. More preferably, the buffer is an organic buffer, such as HEPES, TES, BES, MES, MOPS, or PIPES. Various combinations of oxidizing agents, buffering agents, and chelating agents can be used in such compositions.

In a particularly preferred embodiment, tissue such as porcine aortic root tissue is dissected from the hearts of animals and then shipped on ice in order to reduce autolytic damage to the tissue and to minimize bacterial growth during shipment. Preferably, either at the site of slaughter or shortly thereafter prior to significant tissue damage and/or degradation, the tissue can be treated according to the method of the present invention. For example, the tissue can be immersed in a saline solution (preferably, normal saline at a concentration of about 0.8% to about 1.0% by weight) containing about 20 millimolar (mM) to about 30 mM EDTA or EGTA, about 10 mM to about 30 mM HEPES, and a concentration of sodium hypochlorite (5% stock bleach solution) of no less than about a 1:400 dilution or no more than about 1:50 of stock bleach (which generally corresponds to about 2 mM to about 20 mM). The tissue preferably remains immersed in the bleach solution for a period of no less than about 24 hours, and more preferably, no more than about 36 hours, at room temperature.

Prior to or subsequent to contacting the tissue with the composition containing the oxidizing agent, the tissue is preferably contacted with a detergent composition. More preferably, this includes contacting the tissue with a first detergent composition and then a second detergent composition. Preferably, the first detergent composition includes an ionic detergent and the second detergent composition includes a nonionic detergent. Preferably, these steps are carried out at a temperature of at least about 30° C. In certain embodiments, these steps involve sonicating the tissue while in the detergent compositions at a temperature of about 30° C. to about 45° C.

Proteins suspected of being involved in the initial events of calcification are not necessarily accessible due to their tertiary structure, which may hide groups. Therefore, the use of reducing agents may be employed because they can be effective in inactivating proteins with biological activity. Thus, for certain preferred embodiments, the detergent composition can include a reducing agent such as DTT and others that are capable of reducing disulfide bonds.

Another preferred embodiment is directed to a method for reducing mineralization of a tissue-derived implantable medical device. The method involves: contacting the tissue with a composition including at least one oxidizing agent; rinsing the tissue to remove at least a portion of the oxidizing agent; and contacting the tissue with a detergent composition including at least one reducing agent prior to implantation of the medical device.

Yet another preferred embodiment is directed to a method for reducing mineralization of a tissue-derived implantable medical device. The method involves: contacting the tissue with a non-phosphate buffered organic saline solution; contacting the tissue with a composition including at least one oxidizing agent; rinsing the tissue to remove at least a portion of the oxidizing agent; contacting the tissue with a first detergent composition including at least one ionic detergent and at least one reducing agent; rinsing the tissue to remove at least a portion of the first detergent composition; and contacting the tissue with a second detergent composition including at least one nonionic detergent and at least one reducing agent prior to implantation of the medical device.

The compositions used in the present invention are all typically aqueous based. Furthermore, the treatment steps of the present invention can be carried out in any order desired. For example, tissue can be treated with a composition containing an oxidizing agent followed by one or more detergent compositions, with or without a reducing agent, followed by fixing the tissue. Alternatively, tissues can be treated with a detergent composition, with or without a reducing agent, followed by an oxidizing agent, followed by a second detergent composition, with or without a reducing agent, followed by fixing. Or, the fixation process (using a glutaraldehyde- or a carbodiimide-based process, for example) can be carried out first, e.g., prior to contacting the tissue with an oxidizing agent or a detergent composition.

As used herein, a "tissue-derived implantable medical device" is meant to include an organ or tissue that is derived in whole or part from an animal, typically a mammal, or which is made from other organic tissue and is to be implanted alone or as part of a bioprostheses. Thus, the term generally includes bioprosthetic tissue, such as hearts, heart valves, aortic root tissue and other heart components, pericardium, vascular replacements, e.g., veins and/or arteries, or grafts, heart replacements, urinary tract and bladder replacements, bowel and tissue resections in general, and the like.

As used herein, the term "pathologic calcification" refers to the undesirable deposition of calcium phosphate mineral salts. Without being bound by any theory or mechanism, calcification may be due to host factors, implant factors, and other patient-related extraneous factors. There is evidence to suggest that deposits of calcium are related to devitalized cells and, in particular, cell membranes having calcium channels that are no longer functioning or are malfunctioning. Calcification has been observed to begin with an accumulation of calcium and phosphorous, present under the appropriate conditions of concentration and molecular alignment to form hydroxyapatite, which develops into nodules that can eventually lead to valvular failure in a tissue-derived implantable device.

As used herein, the term "reduced mineralization" refers to a quantitative decrease in the observed accumulation of minerals, such as calcium phosphate mineral salts, to a tissue-derived implantable medical device of the invention and refers preferably to the aortic walls and leaflets of such devices.

DETAILED DESCRIPTION OF PREFERRED EMBODIMENTS

1. Procurement and Initial Treatment of Tissue

A tissue-derived implantable medical device employed in a method of the invention can be obtained from a mammalian species. Mammalian species suitable for providing tissue for a tissue-derived implantable medical device in the invention, include, for example, pigs, cows, sheep, etc. Preferably, the mammalian species is a pig or a cow. Preferred tissues for use in the present method include, for example, porcine aortic root tissue, bovine aortic root tissue, porcine and/or bovine pericardium or veins and arteries. Preferably, the tissue-derived implantable medical device contains a heart valve.

Typically, the tissue for a tissue-derived implantable medical device is obtained directly from a slaughter house, dissected at the slaughter house to remove undesired surrounding tissue. Either at the site of slaughter or shortly thereafter prior to significant tissue damage and/or degradation, the tissue is treated according to the present invention. It can be treated by the various steps of the invention in any of a wide variety of orders.

In a typical situation, once the tissue is obtained it is shipped on ice in order to reduce autolytic damage to the tissue and to minimize bacterial growth during shipment. Preferably, the tissue is shipped and received within about 24 hours to a location where treatment of the tissue, as described herein, can be performed.

In one method, the tissue is thoroughly rinsed with a non-phosphate buffered organic saline solution. The non-phosphate buffered organic saline solution stabilizes the tissue matrix while assisting in the removal of excess blood and body fluids that may come in contact with the tissue. A non-phosphate buffered organic saline solution is preferred in the present method as it serves to remove phosphate containing material in the tissue-derived implantable medical device.

Suitable buffering agents for the non-phosphate buffered organic saline solution used in the practice of the invention are those buffering agents which have a buffering capacity sufficient to maintain a physiologically acceptable pH and do not cause deleterious effects to the tissue-derived implantable medical device. Preferably, the non-phosphate buffered organic saline solution includes a buffering agent in a concentration of about 10 mM to about 30 mM. Buffering agents include, for example, acetate, borate, citrate, HEPES (N-2-hydroxyethylpiperazine-N'-2-ethanesulfonic acid), BES (N,N-bis[2-hydroxyethyl]-2-amino-ethanesulfonic acid), TES (N-tris[Hydrpxymethyl]methyl-2-aminoethanesulfonic acid), MOPS (morpholine propanesulphonic acid), PIPES (piperazine-N,N'-bis[2-ethane-sulfonic acid]), or MES (2-morpholino ethanesulphonic acid), and typically provides buffering in a pH range of about 6.5 to about 8.5. An organic buffer is preferred as it will typically not add additional phosphate to the tissue matrix, which may participate in the formation of hydroxyapatite as do other physiologic buffers known in the art, such as sodium phosphate. Organic buffers also provide a means of buffering solution without interfering with subsequent crosslinking chemistry. Preferably, the buffering agent is HEPES, TES, BES, MOPS, PIPES, or MES. More preferably, the buffering agent employed in a saline solution of the invention is HEPES, as it provides a pKa of about 7.4, which is very suitable for tissue processing.

Employing a non-phosphate buffered organic saline solution typically decreases the likelihood of a nucleation event. Using phospate salts to buffer solutions may increase the levels of phospate, $PO_4^{3-}$, to the point that it will bind available divalent cations such as calciumn, thus creating an environment prone to precipitate calcium phospate salts. Excessively high phosphate and calcium levels have been used in in vitro calcification models. Depriving such matrices of these elements will forestall early nucleation events from occurring during tissue processing procedures, as nucleation may have long term effects after the tissue is fixed and stored prior to implantation. Thus, preferably, in a first treatment step a dissected tissue is treated as quickly as possible, typically within 24 hours, with a non-phosphate buffered organic saline solution of the invention. Early treatment of the tissue is preferred as this allows better diffusion of soluble ions such as calcium, phospate, magnesium, divalent cations, and anionic compounds, in general, out of the tissue. These elements are primary components of dystrophic mineralization, in general, and calcification, specifically.

The non-phosphate buffered organic saline solution suitable for use in the present invention typically contains additional components, which include, for example, a saline solution, preferably, of about 0.8% to about 1.0% by weight. Additionally, the non-phosphate buffered organic saline solution preferably contains a chelating agent. The chelating agent is preferably present in the solution at a concentration of about 20 mM to about 30 mM. Suitable chelating agents include, for example, EDTA (ethylenediaminetetraacetic acid), EGTA (ethylenebis(oxyethylenenitrilo)tetraacetic acid), ethylenebis(oxyethylenenitrilo)tetraacetic acid, citric acid, or salts thereof, and sodium citrate. A chelating agent employed in a method of the invention preferably binds divalent cations, such as calcium, magnesium, zinc, and manganese. Removal of such ions from the tissue-derived implantable medical device during initial processing may render the tissue less susceptible to spontaneous precipitation of these divalent ions with phosphate ions that may be present in the tissue. Thus, taking away these divalent cations will prevent apatite formation.

In a preferred embodiment, the non-phosphate buffered organic saline solution of the invention is about 0.9 wt-% saline, buffered to a pH of about 7.4 with about 10 (millimolar) mM to about 30 mM HEPES buffer and contains about 20 mM to about 30 mM of EDTA. Subsequent to rinsing in the non-phosphate buffered organic saline solution, as described above, the tissue-derived medical device may be maintained at about 4° C. for about 4 hours to about 16 hours until further processing.

2. Subsequent Treatment, Transport, and Storage of the Tissue

After the tissue-derived implantable medical device has been rinsed and stored prior to shipment, the procured tissue is preferably transferred and immersed in a composition containing an oxidizing agent. Alternatively, the tissue can be immediately rinsed and stored in a composition containing an oxidizing agent. This composition can be used to transport the tissue from the slaughterhouse to the manufacturing facility.

The composition includes one or more oxidizing agents. Typically, oxidizing agents are capable of accepting electrons, although in this particular system they may not be functioning in that capacity. Preferably, the oxidizing agent is selected from the group of sodium hypochlorite, sodium bromate, sodium hydroxide, sodium iodate, sodium periodate, performic acid, periodic acid, potassium dichromate, potassium permanganate, chloramine T, peracetic acid, and combinations thereof. More preferably, the oxidizing agent is selected from the group of sodium hypochlorite, performic acid, periodic acid, peracetic acid, and combinations thereof. The oxidizing agent is preferably in the composition in an amount of about 2 mM to about 20 mM, and more preferably, about 5 mM to about 10 mM.

The composition also preferably includes a chelating agent, as described above, and also preferably includes a buffering agent and a saline solution in the concentrations described above. Preferably, the buffering agent has a pKa of about 6.5 to about 7.5. More preferably, the buffering agent is an organic buffer, such as HEPES, TES, BES, or others as described above. Preferably, the tissue is immersed in a 0.9% saline solution (normal saline) containing about 20 TnM to about 30 mM EDTA, about 10 mM to about 30 mM HEPES, and a concentration of sodium hypochlorite (5% stock bleach solution) of no less than about a 1:400 dilution or no more than about 1:50 of stock bleach (which generally corresponds to about 2 mM to about 20 mM). The tissue preferably remains immersed in the bleach solution for a period of no less than about 24 hours, and more preferably, no more than about 36 hours, at room temperature.

The composition containing an oxidizing agent, such as sodium hypochlorite may act to "inactivate" the activity of specific proteins such as kinases, phospatases and others within the tissue matrices that may be essential for the initiation of the calcification process. It is thought that the use of oxidizing agents in the composition may inhibit biological functions of protein structure. For example, the oxidation of specific —R groups of amino acid side chains may interrupt the folding of specific proteins, thus disrupting the native conformation of the enzyme, rendering it unable to process substrate.

Although not wishing to be bound by theory, it is believed that the oxidizing agent uncouples enzymatic reactions that occur within cells that reside in the extra-cellular matrix (ECM). These enzymes utilize calcium and phosphate in a variety of energy utilization and cell signaling mechanisms. Under the proper conditions, that may be present during tissue processing, these enzymes may be responsible for sequestering the ions necessary to form apatite (i.e., hydroxyapatite) in the ECM. Other reactions can take place besides the modification of protein active sites. Disulfide bonds that may exist in specific proteins may be broken, resulting in protein dysfunction by altering its tertiary structure.

Compositions containing one or more oxidizing agents may work on reducing sugars present in glycosaminoglycans such as heparin, chondroitin sulfate, dermatin sulfate. The oxidative process could yield these compounds susceptible to crosslinking. This solution can also be considered a bacteriocidal solution and will inhibit the growth of bacteria in the solution during transport. A tissue-derived implantable medical device placed in the composition containing an oxidizing agent described above, can be stored and/or shipped as desired.

3. Additional Processing of the Tissue

Preferably, subsequent to treatment with the composition containing an oxidizing agent as described above, the tissue-derived implantable medical device is rinsed exhaustively with a non-phosphate buffered organic saline solution described above to completely remove the oxidizing agents. Preferably, the tissue-derived implantable medical device is rinsed at room temperature for about 8 to about 18 hours. Preferably, the non-phosphate buffered organic saline solution is changed frequently, e.g., about every 20 to about 30 minutes. The frequent solution change can equate to about a 32-volume change, i.e., approximately 250 mL per volume change, during the course of the rinse treatment.

Regardless of the specific rinse treatment protocol employed, the tissue to non-phosphate buffered organic saline solution ratio, i.e., tissue to volume ratio, should be fairly large. A large tissue to volume ratio employed in the method is designed to create the largest possible gradient for solute diffusion (i.e., removal) out of the tissue ECM and facilitate movement of materials into the surrounding non-phosphate buffered organic saline solution. The frequent volume changes are effective in maintaining the diffusion gradients to assist in the removal of the oxidizing agent from the ECM. During the rinse treatment described herein, the tissue may optionally be subjected to ultrasonic processing using a sonicator. Employing a sonicator may be advantageous in that it may further assist in the diffusion of materials from the tissue.

Additionally, the temperature during the rinse treatment described above is preferably maintained at less than about 45° C. Maintaining the temperature of the rinse treatment can be accomplished by employing a heat exchange system in combination with the ultrasonic processing. The heat exchange system involves pumping the detergent composition from a reaction vessel (containing the tissue) into a stainless steel coil immersed in a water bath (heat exchanger), preferably at a temperature of about 35° C. to about 45° C., and back into the reaction vessel.

4. Treatment of the Tissue with a Detergent

Preferably, after the tissue is thoroughly rinsed, thus ensuring removal of the oxidizing agent, the tissue is immersed in a first composition containing at least one detergent. Preferably, the detergent is an ionic detergent such as sodium dodecyl sulfate (SDS), although numerous other ionic detergents can be used. Examples include sodium caprylate, sodium deoxycholate, and sodium 1-decanesulfonate. The concentration of ionic detergent is preferably within a range of about 0.5% to about 2.5% (weight by volume for solids or volume by volume for liquids), and more preferably, about 0.5% to about 1.5% (weight by volume for solids or volume by volume for liquids). The detergent composition preferably also contains about 10 to about 30 mM HEPES (or other buffer as described above), about 20 mM to about 30 mM EDTA (or other chelating agent as described above), and saline in an amount of about 0.8% to about 1.0% (by weight).

The solution may also optionally contain a reducing agent such as DTT (dithiothreotol) (or similar such agents) in a range of 10 mM to about 200 mM. Examples of other suitable reducing agents include, for example, 2-mercaptoethylamine and DTE (dithioerythritol). Reducing agents also have the potential to inactivate proteins and such treatment alters the tertiary structure of bioactive compounds and makes them inactive. Alternatively, the tissue can be treated with an aqueous solution containing the reducing agent and other optional components without a detergent.

The tissue is subsequently placed in the first detergent containing composition for a period of at least about 24 hours at a temperature of at least about 30° C. The temperature at which this process takes place can have a significant effect on the ability of detergents to gain access to phospholipids of the cell membranes and associated proteins to be removed or modified. It is known that when phospholipid bilayers are heated they undergo changes in physical properties over specific temperature ranges. This "phase transition" is due to the increased motion about the carbon-carbon bonds of fatty acyl chains. The acyl chains pass from a highly ordered, gel-like state at cooler temperatures (i.e., room temperature) to a more mobile fluid state at higher temperatures. During the gel-to-fluid transition, thermal energy is absorbed and the bilayer passes through the "melting temperature" of the bilayer. The fluidity of the membrane bilayers at the temperatures used in this process allow for greater ease of dissolution of the cell membranes.

During the treatment of the tissue with a detergent, the tissue may be subjected to ultrasonic processing as described above. The temperature during this treatment is typically maintained at less than about 50° C., and preferably, less than about 45° C., using a heat exchange system in combination with the ultrasonic system, for example.

The detergent is used to facilitate the removal of cells, cell debris, and cell organelles from the ECM. Cell membranes and cell organelle membranes are known to house a large part of the enzymes and proteins implicated in the nucleation of apatite formation during the mineralization process. Solubilization of these membranes may also assist in the inhibition of calcification by denaturing the proteins during the extraction process. It has also been proposed that phospholipids, which make up the largest portion of cell membranes, are involved in the initiation of calcification. Detergent treatments will break up the phospholipid bilayer of cell membranes in the process of extracting the proteins.

After treatment with the detergent composition, the tissue-derived implantable medical device is typically processed through another exhaustive rinse process utilizing the non-phosphate buffered organic saline solution described above. After rinsing, the tissue-derived implantable medical device is placed into a second detergent composition. The second detergent composition preferably contains a greater affinity for phospholipids than the first detergent composition discussed above. Preferably, the second detergent composition contains the detergent NP-40, although other nonionic detergents can be used such as Triton X-100, Tween series, and octylglucoside. The use of this detergent is designed to further assist in the removal of cellular material and debris.

This second detergent composition preferably also contains about 10 to about 30 mM HEPES (or other buffer as described above), about 20 mM to about 30 mM EDTA (or other chelating agent as described above), and saline in an amount of about 0.8% to about 1.0% (by weight). This detergent may also have a reducing agent as described above in the first detergent composition. The detergent concentrations employed in the second detergent containing composition are similar to the detergent concentrations employed in the first detergent containing composition, with the standard concentration used preferaby being about 0.5% to about 2.5% (volume by volume for liquids), and more preferably about 0.5% to about 1.5% (volume by volume for liquids). The nonionic detergents described herein may act in different ways at varying concentrations. For example, at high concentrations (above the critical micelle concentration) nonionic detergents solubilize biological membrane by forming mixed micelles of detergents, phospholipid, and integral membrane proteins. At low concentrations, nonionic detergents may bind to the hydrophobic regions of most membrane proteins, making them soluble in aqueous solutions.

Typically, the tissue-derived implantable medical device is placed in the second detergent containing composition for a period of at least about 24 hours at a temperature of at least about 30° C. During this stage of the process, the tissue-derived implantable medical device, as described above, may be subjected to ultrasonic processing. As further described above, the temperature is typically maintained at less than about 50° C., and preferably, less than about 45° C., using a heat exchange system in combination with the ultrasonic system.

After treatment with the second detergent containing composition, the tissue-derived implantable medical device is rinsed exhaustively in the non-phosphate buffered organic saline solution described above for about 24 hours at room temperature (e.g., about 25° C. to about 30° C.). At the completion of the rinse treatment, the tissue-derived implantable medical device may be placed in the non-phosphate buffered organic saline solution and stored at 4° C. until the fixation process.

One of skill in the art will appreciate that the order of the use of the detergent containing compositions may be changed. That is, treatment of a tissue-derived implantable medical device with a nonionic detergent containing composition can be used prior to treatment of the tissue-derived implantable medical device with an ionic detergent containing composition. Moreover, the method described herein is specifically designed to be modular, in that particular treatment steps can be placed anywhere within the tissue-derived implantable medical device processing procedure. For example, a detergent may be used in a transport solution prior to the exposure of the oxidizing agents, followed by another detergent treatment.

5. Fixation of the Tissue

Preferably, after detergent treatment and rinsing treatment as described above, fixation of the tissue, although fixation could occur before any treatment steps described herein. Typically, prior to fixation, the tissue-derived implantable medical device is rinsed with a non-phosphate buffered organic saline solution similar to the non-phosphate buffered organic saline solution described above, however, the buffering agent, such as HEPES, is employed at concentration of about 10 mM to about 20 mM. Two alternative fixation treatments to preserve the tissue-derived implantable medical device can be employed in the method of the present invention. A first fixation treatment employs a cross-linking process which introduces the tissue-derived implantable medical device to about a 0.2% glutaraldehyde solution in the prepared non- phosphate buffered organic saline solution described above. This fixation process takes approximately 7 days to complete, and is well known to one of skill in the art.

A second fixation treatment employs a cross-linking process which introduces the tissue-derived implantable medical device to about a water soluble carbodiimide as disclosed in U.S. Pat. No. 5,447,536 (Giardot et al.) and U.S. Pat. No. 5,733,339 (Giardot et al.) and EP 897942 A (Cahalan et al.). This fixation process is a two-stage process that utilizes more of the available side groups on the amino acid backbone of the collagen molecules.

The following examples more fully describe the present invention. Those skilled in the art will recognize that the particular reagents, equipment and procedures described are merely illustrative and are not intended to limit the present invention in any manner.

EXAMPLE

Enzyme Activity Related to Various Alternative Tissue Process Treatments

I. Background

Current treatments for the inhibition of calcification do not offer total protection for both leaflet and wall. Based on published reports in the literature the initiation events of calcification are most certainly cellular based. The exact mechanism for this nucleation event is unknown but may involve proteins that are involved in the use of calcium and/or phosphate in signal transduction, energy utilization, post transnational modifications of proteins or ion balance within a cell.

In an attempt to understand if these first steps could be involved in nucleation events, proteins were used to test the theory of inactivating their function by denaturation. The model system utilizes proteases to test the function of protein after treatment. These proteins are assisted in maintaining their tertiary structure by different bonding mechanisms, trypsin by hydrogen bonds and chymotrypsin by a combination of disulfide bonds and hydrogen bonds.

In these experiments trypsin and chymotrypsin were chosen based on their ability to digest a collagen based substrate (AZOCOLL, Sigma Chemical) that liberates a colored byproduct after enzymatic attack.

II. Summary

Trypsin and chymotrypsin were subjected to several denaturation/inactivation methodologies, either by exposure to oxidizing agents, reducing agents, or detergent(s). The preliminary data indicates that denaturing can inactivate these proteins by modifying their tertiary structure.

III. Materials

Phosphate Buffered Saline (PBS), Sigma product no. 1000-3, Sigma Chemical Co., St. Louis, Mo.

Normal Saline (NS), Sigma 430AG-4, Sigma

AZOCOLL (Azo dye impregnated collagen, product no. 194933) Calbiochem, San Diego, Calif.

Sodium hypochlorite (Bleach)

Peracetic acid, Aldrich Chemical Co., Milwaukee, Wis.

SDS, Sigma product no. L 4509, Sigma Chemical

Trypsin (Type I, bovine pancreas, product no. T 4665), Sigma

Chymotrypsin (bovine pancreas, product no. C 4129), Sigma

DTT (dithiothreatol, product no. D 0632), Sigma

Water bath

Spectrophotometer (Beckman Model)

IV. Methods

Protein Preparation

Because of the sensitivity of these enzymes to auto-digestion all protein solution were made fresh on the day of the experiment and stored on ice until use.

Stock trypsin and chymotrypsin solutions were solubilized from dry powder supplied by the manufacturer in PBS, pH 7.4, at room temperature. Protein concentrations were set at 1 mg/ml. Protein solutions were sterile filtered through a 0.45 µm syringe filter to eliminate potential bacterial contamination.

Working solution of the protein was prepared by dilution from concentrated stock to a final concentration of 100 µg/ml.

Protein Treatment

Each of the proteins was exposed to various agents under the following conditions.

Oxidizing agents: Proteins were exposed to either peracetic acid or bleach for a period of 2 hours at room temperature. After treatment the proteins were passed over a desalting column (Sephadex G-25) to separate the oxidizing agent from the protein. Protein was eluted from the column using PBS. Elution of the protein was tracked by monitoring UV absorbance at 280 nm. The eluted protein was harvested in 0.5 ml aliquots. The aliquots that had the highest UV absorbance were used for the analysis.

Reducing agents: Chymotrypsin was exposed to DTT (final concentration 10 mM PBS, pH 7.4) in the presence of SDS (1% w:v). The protein was incubated with the agents for 2 hours. In order to assure all disulfide bonds were acted on and fully reduced, the reaction was performed at elevated temperature (37° C.–40° C.). The protein was passed over a Sephadex G-25 column, as described above, to prepare it for the assay. After the protein was eluted from the column it was used immediately in the assay.

Denaturing: Trypsin was exposed to SDS (final concentration 1% w:v in PBS, pH 7.4). The protein was prepared for the assay by dialyzing against PBS to remove excess SDS. Dialysis was performed at 4° C. to minimize auto-digestion.

Enzyme Activity Assessment

Each of the proteins that were exposed to an agent was assessed for its activity by incubating it with a collagen substrate with an azo containing dye. AZOCOLL was suspended in PBS at a concentration of 1 mg/ml.

For the assay, I ml of protein was mixed with 1 ml of AZOCOLL substrate. The reaction was performed at 37° C. for 20 minutes in Ependorff microfuge tubes. At the end of the reaction time, the reaction was terminated by centrifuging the mixture, separating the undigested AZOCOLL from the aqueous solution. The aqueous solution was removed from the centrifuge tubes and the absorbance of the solution (containing soluble azo dye) was monitored at 520 nm.

Controls consisted of a negative control, which was PBS containing the appropriate agent employed to act on the protein, but without the protein itself. Positive controls were enzymes that were not exposed to the treatments. They were aliquoted directly from the stock solution into the AZOCOLL reaction vessel.

Data Analysis

All experiments were run in triplicate. Data reported is the mean of the 3 readings. The experiments were done to test feasibility of the model system; no attempt was made to do statistical analysis on or between the various groups.

V. Results

Trypsin exposure to oxidizing agent(s)

| Sample | Abs. @ 520 nm |
|---|---|
| Negative control | 0.089 |
| Positive control | 0.664 |
| Treated sample | 0.342 |

Trypsin exposure to denaturing agent (SDS)

| Sample | Abs. @ 520 nm |
| --- | --- |
| Negative control | 0.004 |
| Positive control | 0.544 |
| Treated sample | 0.066 |

Chymotrypsin exposed to reducing agent

| Sample | Abs. @ 520 nm |
| --- | --- |
| Negative control | 0.003 |
| Positive control | 0.523 |
| Treated sample | 0.031 |

VI. Discussion

The data suggests that the treatments above may be helpful in inactivating proteins within the extracellular matrix of tissue. There are several points that need to be evaluated before a model is adopted and considered reliable for evaluating subsequent tissue matrix treatments. The first is the appearance of reacted substrate in the negative controls. This may mean that, in the case of oxidizing agents that there is some possible reaction occurring by association of the reagents.

For the other experiments utilizing SDS, the low backgrounds may be due to excess SDS that is carried into the assay from the enzyme exposed to the reaction. The SDS may bind to the AZOCOLL making it less susceptible to degradation.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method of making a tissue-derived, implantable vascular bioprosthesis, the method comprising:
   excising tissue from an animal, the excised tissue selected form the group consisting of porcine aortic toot tissue, bovine aortic root tissue, porcine pericardium, bovine pericardium, bovine veins, porcine veins, bovine arteries, and porcine arteries; and removing cell debris from the excised tissue by a method which comprises: contacting the excised tissue with a composition comprising at least on oxidizing agent prior to significant degradation of the excised tissue; and rinsing the oxidizing agent-contacted tissue to remove at least a portion of the oxidizing agent, wherein the oxidizing agent is selected from the group of sodium hypochlorite, performic acid, periodic acid, peracetic acid, and combinations thereof.

2. The method of claim 1 wherein the sodium hypochlorite is in a concentration of about 2 mM to about 20 mM.

3. The method of claim 1 wherein the composition comprising an oxidizing agent further comprises at least one chelating agent.

4. The method of claim 3 wherein the chelating agent is selected from the group of ethylenediaminetetraacetic acid, ethylenebis(oxyethylenenitrilo)tetraacetic acid (EGTA), citric acid, salts thereof, and combinations thereof.

5. The method of claim 1 wherein the composition comprising at least one oxidizing agent further comprises at least one buffering agent.

6. The method of claim 5 wherein the buffering agent has a pKa of about 7.0 to about 7.5.

7. The method of claim 5 wherein the buffering agent is an organic buffer.

8. The method of claim 7 wherein the buffering agent is selected from the group of HEPES, TES, BES, MOPS, PIPES, MES, and combinations thereof.

9. The method of claim 1 wherein contacting the tissue with a composition comprising at least one oxidizing agent is carried out for at least about 24 hours.

10. The method of claim 1 wherein the rinsing step includes contacting the tissue with a detergent composition.

11. The method of claim 10 wherein the detergent composition comprises at least one reducing agent.

12. The method of claim 10 wherein the detergent composition comprises an ionic detergent or a nonionic detergent.

13. The method of claim 10 wherein contacting the tissue with the detergent composition is carried out at a temperature of at least about 30° C.

14. The method of claim 10 wherein contacting the tissue with the detergent composition comprises sonicating the tissue while immersed in the composition.

15. The method of claim 10 wherein contacting the tissue with a detergent composition comprises contacting it with a first and a second detergent composition.

16. The method of claim 15 wherein the first detergent composition comprises an ionic detergent and the second detergent composition comprises a nonionic detergent.

17. The method of claim 16 wherein the first and/or the second detergent compositions comprise at least one reducing agent.

18. The method of claim 1 further comprising treating the rinsed tissue with a fixative composition.

19. The method of claim 18 wherein treating the tissue with a fixative composition comprises using a glutaraldehyde- or a carbodiimide-based process.

20. The method of claim 19 wherein the fixative composition further comprises at least one buffering agent.

21. A method for making a tissue-derived implantable medical device from freshly excised tissue of an animal, the method comprising:
   excising fresh tissue from an animal, the tissue selected from the group consisting porcine aortic root tissue, bovine aortic root tissue, porcine pericardium, bovine pericardium, bovine veins, porcine veins, bovine arteries, and porcine arteries;
   contacting the freshly excised tissue with a composition comprising at least one oxidizing agent prior to significant degradation of the excised tissue, wherein the oxidizing agent is selected from the group of sodium hypochlorite, performic acid, periodic acid, peracetic acid, and combinations thereof;
   rinsing the oxidizing agent-contacted tissue to remove at least a portion of the oxidizing agent; and
   contacting the rinsed tissue with a composition comprising at least one reducing agent.

22. The method of claim 21 wherein the sodium hypochlorite is in a concentration of about 2 mM to about 20 mM.

23. The method of claim 21 wherein the composition comprising an oxidizing agent further comprises at least one chelating agent.

24. The method of claim 23 wherein the chelating agent is selected from the group of ethylenediaminetetraacetic acid, ethylenebis(oxyethyleneitrilo)tetraacetic acid (EGTA), citric acid, salts thereof, and combinations thereof.

25. The method of claim 21 wherein the composition comprising at least one oxidizing agent further comprises at least one buffering agent.

26. The method of claim 25 wherein the buffering agent has a pKa of about 7.0 to about 7.5.

27. The method of claim 25 wherein the buffering agent is an organic buffer.

28. The method of claim 27 wherein the buffering agent is selected from the group of HEPES, TES, BES, MOPS, PIPES, MES, and combinations thereof.

29. The method of claim 21 wherein contacting the tissue with a composition comprising at least one oxidizing agent is carried out for at least about 24 hours.

30. The method of claim 21 also comprising contacting the reducing agent-contacted tissue with a detergent composition.

31. The method of claim 30 wherein the detergent composition comprises an ionic detergent or a nonionic detergent.

32. The method of claim 30 wherein contacting the tissue with the detergent composition is carried out at a temperature of at least about 30° C.

33. The method of claim 30 wherein contacting the tissue with the detergent composition comprises sonicating the tissue while immersed in the composition.

34. The method of claim 30 wherein contacting the tissue with a detergent composition comprises contacting it with a first and a second detergent composition.

35. The method of claim 34 wherein the first detergent composition comprises an ionic detergent and the second detergent composition comprises a nonionic detergent.

36. The method of claim 21 further comprising treating the reducing agent contacted-tissue with a fixative composition.

37. The method of claim 36 wherein treating the tissue with a fixative composition comprises using a glutaraldehyde- or a carbodiimide-based process.

38. The method of claim 37 wherein the fixative composition further comprises at least one buffering agent.

39. A method of making a tissue-derived heart valve bioprosthesis, the method comprising:
excising heart valve tissue from an animal, the excised tissue including valvular leaflets and supporting structure; and
removing cell debris from the excised tissue by a method which comprises: contacting the excised tissue with a composition comprising at least one oxidizing agent prior to significant degradation of the excised tissue; and rinsing the oxidizing agent-contacted tissue to remove at least a portion of the oxidizing agent, wherein the oxidizing agent is selected from the group of sodium hypochlorite, performic acid, periodic acid, peracetic acid, and combinations thereof.

40. The method of claim 39 wherein the sodium hypochlorite is in a concentration of about 2 mM to about 20 mM.

41. The method of claim 39 wherein the composition comprising an oxidizing agent further comprises at least one chelating agent.

42. The method of claim 41 wherein the chelating agent is selected from the group of ethylenediaminetetraacetic acid, ethylenebis(oxyethylenenitrilo)tetraacetic acid (EGTA), citric acid, salts thereof, and combinations thereof.

43. The method of claim 39 wherein the composition comprising at least one oxidizing agent further comprises at least one buffering agent.

44. The method of claim 43 wherein the buffering agent has a pKa of about 7.0 to about 7.5.

45. The method of claim 43 wherein the buffering agent is an organic buffer.

46. The method of claim 45 wherein the buffering agent is selected from the group of HEPES, TES, BES, MOPS, PIPES, MES, and combinations thereof.

47. The method of claim 39 wherein contacting the tissue with a composition comprising at least one oxidizing agent is carried out for at least about 24 hours.

48. The method of claim 39 also comprising contacting the oxidizing agent-contacted tissue with a detergent composition.

49. The method of claim 48 wherein the detergent composition comprises an ionic detergent or a nonionic detergent.

50. The method of claim 48 wherein contacting the tissue with the detergent composition is carried out at a temperature of at least about 30° C.

51. The method of claim 48 wherein contacting the tissue with the detergent composition comprises sonicating the tissue while immersed in the composition.

52. The method of claim 48 wherein contacting the tissue with a detergent composition comprises contacting it with a first and a second detergent composition.

53. The method of claim 52 wherein the first detergent composition comprises an ionic detergent and the second detergent composition comprises a nonionic detergent.

54. The method of claim 39 further comprising contacting the rinsed tissue with a composition comprising at least one reducing agent.

55. The method of claim 54 further comprising treating the reducing agent contacted-tissue with a fixative composition.

56. The method of claim 55 wherein treating the tissue with a fixative composition comprises using a glutaraldehyde- or a carbodiimide-based process.

57. The method of claim 56 wherein the fixative composition further comprises at least one buffering agent.

* * * * *

UNITED STATES PATENT AND TRADEMARK OFFICE
CERTIFICATE OF CORRECTION

| | | |
|---|---|---|
| PATENT NO. | : 6,509,145 B1 | Page 1 of 1 |
| APPLICATION NO. | : 09/806380 | |
| DATED | : January 21, 2003 | |
| INVENTOR(S) | : Mark W. Torrianni | |

It is certified that error appears in the above-identified patent and that said Letters Patent is hereby corrected as shown below:

Column 13, line 46, that poriton of the claim reading "aortic toot" should read --aortic root--.

Column 13, line 52, that portion of the claim reading "least on oxidizing" should read --least one oxidizing--.

Signed and Sealed this

Tenth Day of July, 2007

JON W. DUDAS
*Director of the United States Patent and Trademark Office*